(12) United States Patent
Lim et al.

(10) Patent No.: US 9,283,090 B2
(45) Date of Patent: Mar. 15, 2016

(54) SPINAL CONSTRUCT AND METHOD

(71) Applicant: Warsaw Orthopedic, Inc., Warsaw, IN (US)

(72) Inventors: Roy K. Lim, Germantown, TN (US); Matthew M. Morrison, Cordova, TN (US); William R. Sears, Warrawee Sydney (AU)

(73) Assignee: Warsaw Orthopedic, Inc., Warsaw, IN (US)

( * ) Notice: Subject to any disclaimer, the term of this patent is extended or adjusted under 35 U.S.C. 154(b) by 198 days.

(21) Appl. No.: 13/946,235

(22) Filed: Jul. 19, 2013

(65) Prior Publication Data

US 2015/0025636 A1    Jan. 22, 2015

(51) Int. Cl.
*A61F 2/44* (2006.01)
*A61F 2/46* (2006.01)
*A61B 17/02* (2006.01)
*A61F 2/30* (2006.01)

(52) U.S. Cl.
CPC ............ *A61F 2/4611* (2013.01); *A61F 2/44* (2013.01); *A61B 2017/0256* (2013.01); *A61F 2002/3038* (2013.01); *A61F 2002/30133* (2013.01); *A61F 2002/30507* (2013.01); *A61F 2002/30604* (2013.01); *A61F 2002/30616* (2013.01)

(58) Field of Classification Search
CPC .............. A61F 2/4611; A61F 2/44; A61F 2002/30133; A61F 2002/3038; A61F 2002/30507; A61F 2002/30604; A61F 2002/30616; A61B 2017/0256

USPC ................ 606/246, 279, 90, 105; 623/17.11, 623/17.15, 17.16
See application file for complete search history.

(56) References Cited

U.S. PATENT DOCUMENTS

| 4,554,914 | A | * | 11/1985 | Kapp et al. ................. 606/86 A |
| 6,106,557 | A | * | 8/2000 | Robioneck et al. ........ 623/17.15 |
| 7,563,281 | B2 | | 7/2009 | Sears et al. |
| 7,744,650 | B2 | * | 6/2010 | Lindner et al. ............. 623/17.14 |
| 8,377,140 | B2 | * | 2/2013 | DeFalco et al. ............ 623/17.16 |
| 2010/0076559 | A1 | | 3/2010 | Bagg et al. |
| 2010/0145456 | A1 | | 6/2010 | Simpson et al. |
| 2013/0035763 | A1 | | 2/2013 | Krueger |

FOREIGN PATENT DOCUMENTS

| EP | 1415624 A1 | 5/2004 |
| WO | 9814142 A1 | 4/1998 |

* cited by examiner

*Primary Examiner* — Pedro Philogene
*Assistant Examiner* — David C Comstock

(57) ABSTRACT

A spinal construct includes a first member including a surface that defines a first cavity and a second cavity. The first member is configured to engage a first vertebral surface. A second member includes a surface that defines a first cavity and a second cavity. The second member is configured to engage a second vertebral surface. The members are spaced and the first cavities are disposed in substantial alignment such that at least one first rod is disposed in the first cavities and the second cavities are disposed in substantial alignment such that a plurality of second rods are disposed in the second cavities and spaced via at least one spacer disposed between the second rods within at least one of the second cavities. Systems and methods are disclosed.

20 Claims, 20 Drawing Sheets

SPINAL CONSTRUCT AND METHOD

TECHNICAL FIELD

The present disclosure generally relates to medical devices for the treatment of musculoskeletal disorders, and more particularly to a spinal construct configured for disposal between spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, a spinal construct is provided. The spinal construct comprises a first member including a surface that defines a first cavity and a second cavity. The first member is configured to engage a first vertebral surface. A second member includes a surface that defines a first cavity and a second cavity. The second member is configured to engage a second vertebral surface. The members are spaced and the first cavities are disposed in substantial alignment such that at least one first rod is disposed in the first cavities and the second cavities are disposed in substantial alignment such that a plurality of second rods are disposed in the second cavities and spaced via at least one spacer disposed between the second rods within at least one of the second cavities. In some embodiments, systems and methods are disclosed.

In one embodiment, in accordance with the principles of the present disclosure, a method for treating a spine disorder is provided. The method comprises the steps of: providing a first member including a surface that defines a first cavity and a second cavity; delivering the first member about vertebral tissue along a substantially posterior approach and adjacent a first vertebral surface; providing a second member including a surface that defines a first cavity and a second cavity; delivering the second member about the vertebral tissue along a substantially posterior approach and adjacent a second vertebral surface such that the first cavities are disposed in substantial alignment and the second cavities are disposed in substantial alignment; spacing the members; disposing at least one first rod in the first cavities; and disposing a plurality of spaced second rods within the second cavities.

BRIEF DESCRIPTION OF THE DRAWINGS

The present disclosure will become more readily apparent from the specific description accompanied by the following drawings, in which.

DETAILED DESCRIPTION

Figure 1:
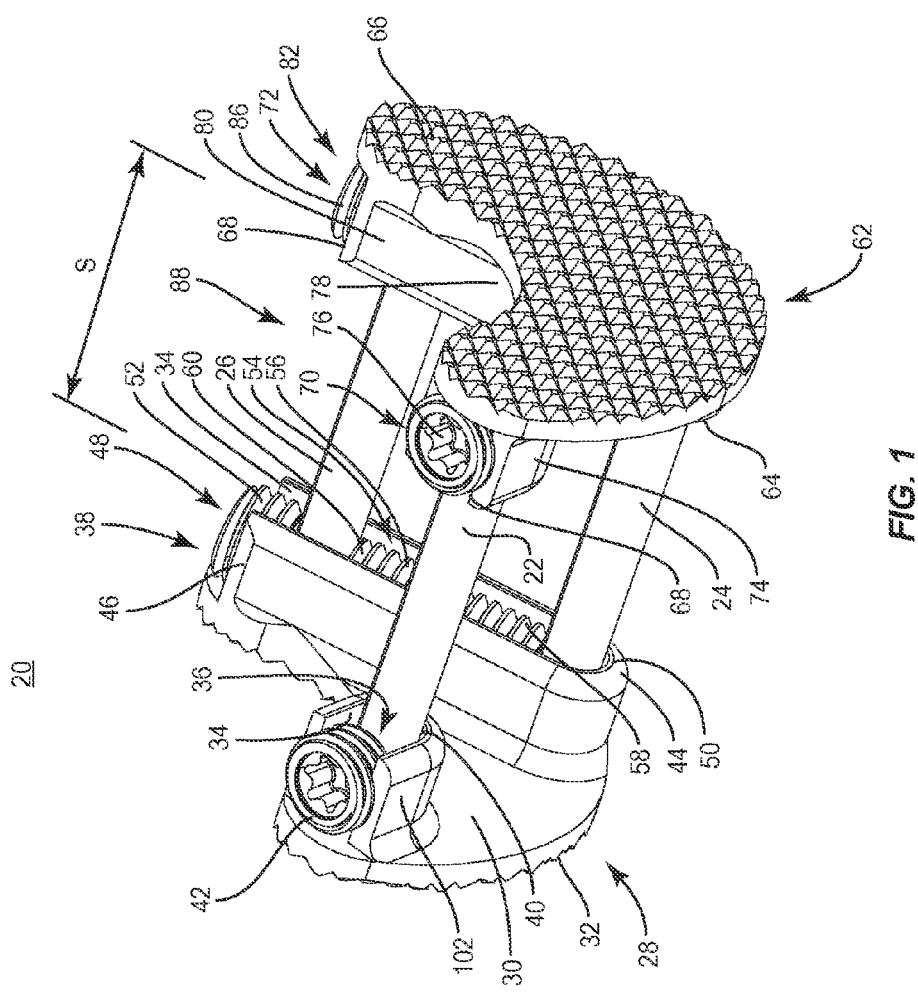
FIG. 1 is a perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a spinal implant system that includes a spinal construct configured for disposal between spaced vertebrae and a method for treating a spine.

In one embodiment, the surgical system includes a posterior corpectomy implant that can be constructed in vivo. In one embodiment, the corpectomy implant includes a first implant, such as, for example, a first horseshoe-shaped endplate and a second implant, such as, for example, a second horseshoe-shaped endplate. In one embodiment, the implant is employed with a method such that the horseshoe-shaped endplates can be maneuvered around exiting nerve roots, under a spinal cord and positioned adjacent a first vertebral body and a second vertebral body. The endplates can be positioned adjacent the first and second vertebral bodies. In one embodiment, the endplates are distracted and rods are placed between the endplates. In some embodiments, the surgical system is low cost, easy to use and preserves peripheral nerves of a spine. In one embodiment, the system includes a spacer nut for spacing two support rods of a spinal construct. In one embodiment, the implant system includes the spacer nut, three support rods and a rack spreader instrument to restore a space between removed vertebral bodies.

In one embodiment, a delivery instrument is engaged to two members, such as, for example, horseshoe-shaped endplates. In one embodiment, a rack spreader is docked to handles of the delivery instrument and locked in place. The rack spreader can be actuated to restore space between first and second vertebral bodies. In one embodiment, a rod is maneuvered under an exiting nerve root and into a saddle at an anterior part of each horseshoe-shaped endplate. In some embodiments, spacers, such as, for example, long screws are used to lock a first rod into position and provide a saddle for a second rod. In one embodiment, the second rod is positioned adjacent long screws and locked in place using a coupling member, such as, for example, a set screw. In some embodiments, the rack spreader and delivery instruments are removed from the endplates. In one embodiment, a third rod is maneuvered into position and set screws secure the third rod in place.

In one embodiment, a corpectomy implant includes 4×4.75 millimeter (mm) horse-shoe shaped endplates that provide for a larger graft pocket area and higher strength. In one embodiment, each endplate has rod recesses for greater torsional strength. In one embodiment, an outer surface of the endplates includes at least one of cross-hatch texturing, engagement-enhancing features, such as, for example, spikes, and a porous titanium coating. In some embodiments, the spikes have a length of from about 0.5 mm to about 3 mm, and preferably a length of about 1.5 mm. In one embodiment, the thickness of each endplate is about 7.25 mm. In one embodiment, the thickness of the spinal implant system measured from an outer spiked surface of the first endplate to an outer spiked surface of the second endplate is about 21 mm.

In one embodiment, the system includes angled inserters having splayed handles to allow the endplates to be closer together during insertion. In some embodiments, an angle or bend in the inserter allows for easier manipulation around the spinal cord and associated anatomy. In one embodiment, the splayed handles have a 20 degree angle relative to one another. In one embodiment, a rack is used to dock onto the splayed handles of the inserters and allows for linear distraction of the endplates. In some embodiments, the size of the components of the surgical system can be adjusted according to the number of vertebral levels to be stabilized. In one embodiment, an instrument is used to manipulate the endplates into position, hold the endplates in alignment with the vertebral bodies, size the rods and/or allow for rod placement. In one embodiment, a delivery instrument, such as, for example, manipulators, are secured to the rack at a fixed angle such that the endplates are in substantial alignment. In one embodiment, an attachment point between the manipulator and the rack may be adjustable such that the manipulator can be rotated or translated relative to the rack. In one embodiment, the manipulator is secured to each endplate via a tongue-in-groove connection.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, system 10 may be employed with surgical procedures, such as, for example, corpectomy and discectomy, which include fusion and/or fixation treatments that employ implants, in accordance with the principles of the present disclosure, to restore the mechanical support function of vertebrae.

System 10 includes a spinal construct 20 having a plurality of longitudinal elements, such as, for example, rods 22, 24 and 26. Each of rods 22, 24, 26 has a cylindrical cross section configuration. In some embodiments, system 10 may include one or a plurality of rods, which may be relatively disposed in a side by side, irregular, uniform, non-uniform, offset and/or staggered orientation or arrangement. In some embodiments, rods 22, 24, 26 can have a uniform thickness/diameter. In some embodiments, rods 22, 24, 26 may have various surface configurations, such as, for example, rough, threaded for connection with surgical instruments, arcuate, undulating, dimpled, polished and/or textured. In some embodiments, the thickness defined by rods 22, 24, 26 may be uniformly increasing or decreasing, or have alternate diameter dimensions along its length. In some embodiments, rods 22, 24, 26 may have various cross section configurations, such as, for example, oval, oblong, triangular, rectangular, square, polygonal, irregular, uniform, non-uniform, variable and/or tapered. In some embodiments, rods 22, 24, 26 may have various lengths.

In some embodiments, the longitudinal element may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the longitudinal element includes movement in a lateral or side to side direction and prevents expanding and/or extension in an axial direction. In some embodiments, all or only a portion of the longitudinal element may have a semi-rigid, rigid or elastic configuration, and/or have elastic properties, such as the elastic properties corresponding to the material examples described above. In some embodiments, the longitudinal element may be compressible in an axial direction.

Spinal construct 20 includes a member, such as, for example, an endplate 28 having a U-shaped configuration, such as, for example, a parabolic configuration. Endplate 28 includes a surface 30 and a surface 32 configured to engage a vertebral surface E1 of a vertebral body V1. Surface 32 is substantially planar. In some embodiments, all or only a portion of surface 32 may be arcuate, concave, convex, undulating and/or angled. In some embodiments, surface 32 can have cross-hatch texturing, spikes, barbs, raised elements, a porous titanium coating, and/or be rough, textured, porous, semi-porous, dimpled and/or polished such that it facilitates engagement with tissue. In some embodiments, the vertebral tissue may include intervertebral tissue, endplate surfaces and/or cortical bone.

Endplate 28 includes a surface, such as, for example, an inner surface 34 that defines a cavity 36 and a cavity 38. Cavities 36, 38 are disposed adjacent surface 30. In some embodiments, cavities 36, 38 are disposed between surfaces 30, 32. Cavity 36 defines a U-shaped passageway 40 configured for disposal of single first rod 22. Passageway 40 is configured for mating engagement with a distal end of a delivery instrument, as described herein. Cavity 36 includes a thread form configured to engage a thread form of a coupling member, such as, for example, a set screw 42 to fix rod 22 within cavity 36. In some embodiments, cavity 36 may be fixed with set screw 42 in alternate fixation configurations, such as, for example, friction fit, pressure fit, locking protrusion/recess, locking keyway and/or adhesive.

Cavity 38 extends between an end 44 and an end 46 defining a linear passageway 48 therebetween. Passageway 48 includes an internal thread form configured for threaded engagement with a spacer 54, as described herein. A plurality of spaced rods, such as, for example, rod 24 and rod 26 are disposed in ends 44, 46 of cavity 38, respectively. End 44 defines a U-shaped passageway 50 configured for disposal of rod 24. End 46 is configured for disposal of a set screw 52, as described herein.

Spinal construct 20 includes a plurality of spacers including spacer 54. Spacer 54 includes a cylindrical element including an outer surface 56 configured for fixed engagement with inner surface 34 of endplate 28. Spacer 54 is disposable with linear passageway 48 between rods 24, 26 such that spacer 54 is fixed relative to inner surface 34 to fix the rods relative to endplate 28. Spacer 54 has a cylindrical cross section configuration and outer surface 56 has an external thread form threadably engageable with passageway 48. In some embodiments, the external thread form may include a single thread turn or a plurality of discrete threads. Spacer 54 has a length that occupies a substantial portion of passageway 48. In some embodiments, spacer 54 occupies a majority of passageway 48. In one embodiment, spacer 54 is configured as a set screw. In some embodiments, spacer 54 is engageable with passageway 48 by alternate fixation configurations, such as, for example, friction fit, pressure fit, expandable, locking protrusion/recess, locking keyway and/or adhesive.

Spacer 54 extends between an end 58 and an end 60. End 58 is engageable with rod 24 and end 60 is engageable with rod 26. End 60 has a concave outer surface such that rod 26 is disposable in flush engagement with spacer 54. In some embodiments, end 60 has various outer surface configurations to enhance engagement of rod 26 with spacer 54, such as, for example, end 60 may include a deformable material, such as, for example, silicone or silicone rubber. In some embodiments, all or only a portion of end 60 of spacer 54 may be variously configured and dimensioned, such as, for example, planar, polygonal, irregular, uniform, non-uniform, staggered, tapered, consistent or variable. A coupling member, such as, for example, set screw 52, shorter in length than spacer 54, is disposed to engage rod 26 within cavity 38. Set screw 52 is matingly engageable with end 46 of cavity 38 such that rod 26 is secured between end 60 of spacer 54 and set screw 52.

Spinal construct 20 includes a member, such as, for example, an endplate 62, similar to endplate 28. Endplate 62 has a U-shaped configuration, such as, for example, a parabolic configuration. Endplate 62 includes a surface 64 and a surface 66 configured to engage a vertebral surface E2 of vertebra V2. Surfaces 30, 64 of endplates 28, 62 are oriented to face one another. Rods 22, 24, 26 are disposed between surfaces 30, 64 of endplates 28, 62 such that endplates 28, 62 are spaced to create and maintain a space S between vertebral surfaces E1, E2.

Endplate 62 includes a surface, such as, for example, an inner surface 68 that defines a cavity 70 and a cavity 72, similar to cavities 36, 38 described above. Cavities 70, 72 are disposed adjacent surface 64. Cavity 70 defines a U-shaped passageway 74 configured for disposal of rod 22. Passageway 74 is configured for detachable engagement with a distal end of a delivery instrument, as described herein. Cavity 70 includes a thread form configured to engage a thread form of a coupling member, such as, for example, a set screw 76 to fix rod 22 within cavity 70. Cavities 36, 70 of each endplate 28, 62 are disposed in substantial alignment such that rod 22 is disposed in cavities 36, 70.

Cavity 72 extends between an end 78 and an end 80 defining a linear passageway 82 therebetween, similar to passageway 48 described above. Rods 24, 26 are disposed with ends 78, 80 of cavity 72, respectively. End 78 defines a U-shaped passageway 84 (FIG. 13) configured for disposal of rod 26. End 80 is configured for disposal of a set screw 86, as described herein. Cavities 38, 72 of endplates 28, 62 are disposed in substantial alignment such that opposite ends of rods 24, 26 are disposed in cavities 38, 72 of endplates 28, 62, respectively.

A spacer (not shown), similar to spacer 54 described above, is disposable with passageway 82 between rods 24, 26 such that the spacer is fixed relative to surface 68 to fix rods 24, 26 relative to member 62. The spacer extends between a first end and a second end. The first end is engageable with rod 24 and the second end is engageable with rod 26. A coupling member, such as, for example, set screw 86, similar to set screws 42, 52 and 76 described above, is disposed to engage rod 26 within cavity 72. Set screw 86 is matingly engageable with end 80 of cavity 72 such that rod 26 is secured between the spacer and set screw 86.

Rods 22, 24, 26 are oriented with endplates 28, 62 to define a graft cavity 88 therebetween. Graft cavity 88 is configured to receive an agent, which may include bone graft (not shown) and/or other materials, as described herein, for employment in a fixation or fusion treatment used, for example, in connection with a corpectomy. In one embodiment, the agent may include therapeutic polynucleotides or polypeptides and bone growth promoting material, which can be packed or otherwise disposed on or about the surfaces of the components of system 10, including endplates 28, 62. The agent may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

System 10 includes a delivery instrument 90 configured for mating engagement with each of cavities 36, 70. Delivery instrument 90 includes a pair of endplate manipulators 92, 94. Manipulators 92, 94 each include a handle 96 and an arm 98 extending from handle 96. Arm 98 includes a hook member 100 configured for disposal about an outer surface 102 of cavity 36. Arm 98 further includes a longitudinal element, such as, for example, a lock rod 104. Lock rod 104 is positionable between a first orientation such that lock rod 104 is disposed within arm 98 and a second orientation such that lock rod 104 protrudes from arm 98. In the second orientation, lock rod 104 is disposable in cavity 36 such that each manipulator 92, 94 captures endplates 28, 62 between lock rod 104 and hook member 100.

System 10 includes a distractor, such as, for example, a rack spreader 106 engageable with delivery instrument 90 and defining a longitudinal axis A1. Rack spreader 106 includes a gear rack 108 having a plurality of teeth 110 that are disposed therealong. Manipulator 92 is engageable with an end 109 of gear rack 108 via a fastening member 112. Fastening member 112 includes a C-clip. In some embodiments, manipulator 92 is fastened to gear rack 108 by various fastening engagements, such as, for example, frictional engagement, threaded engagement, mutual grooves, screws and/or nails. Rack spreader 106 includes a sleeve 114 disposed about gear rack 108. Sleeve 114 is engageable with gear rack 108 between a locked configuration and an unlocked configuration. In the locked configuration, sleeve 114 is in fixed engagement with gear rack 108. In the unlocked configuration, sleeve 114 is translatable relative to gear rack 108 along axis A1. Manipulator 94 is engageable with sleeve 114 via fastening member 112 such that as sleeve 114 translates relative to gear rack 108 along axis A1, manipulator 94 disposed with endplate 62 translates parallel to axis A1 to space vertebral surfaces E1, E2.

Figure 2:
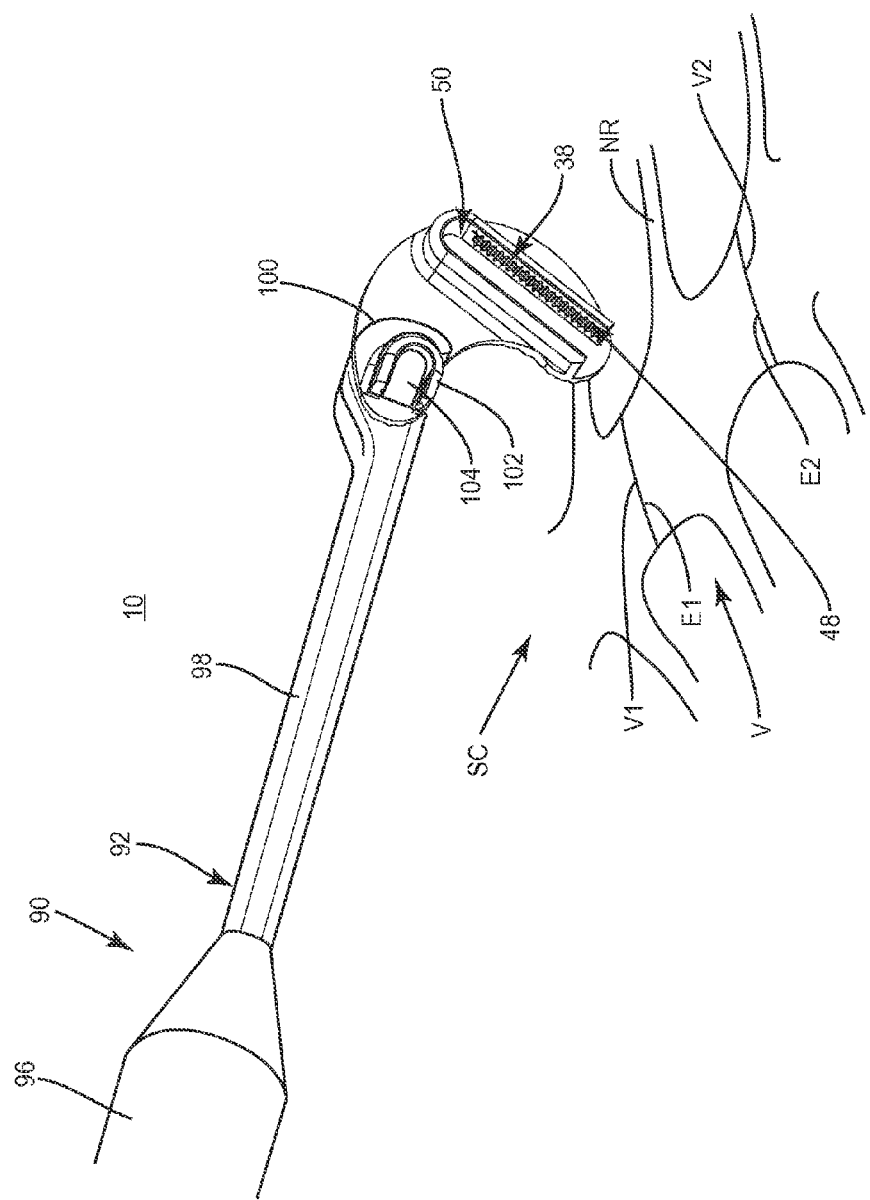
FIG. 2 is a perspective view of components of one embodiment of a spinal implant system in accordance with the principles of the present disclosure disposed with a spine.
Figure 3:
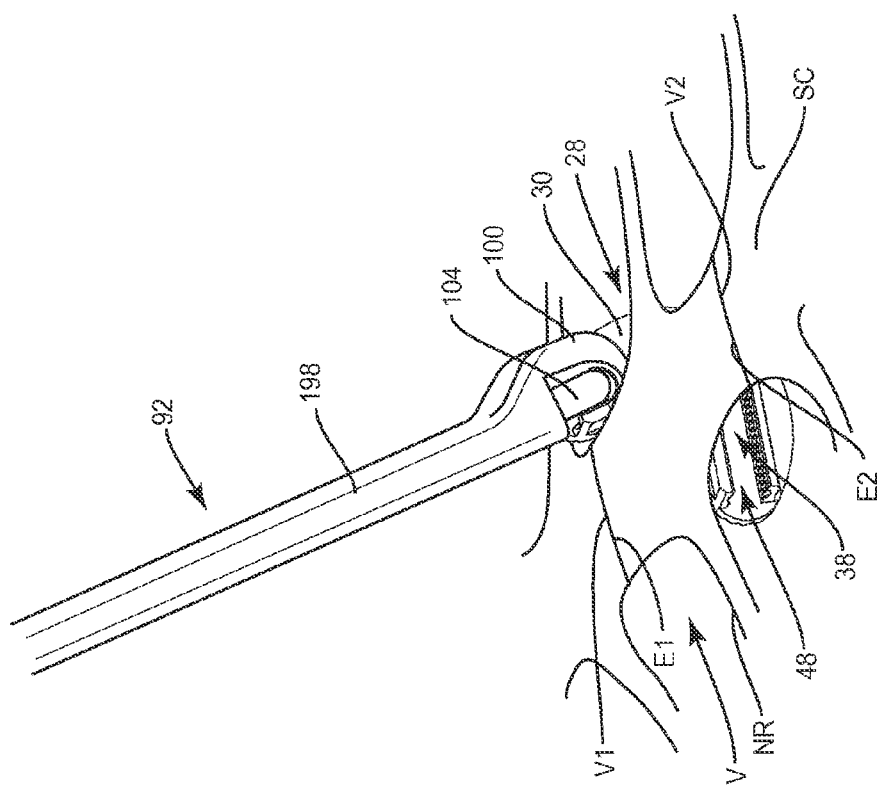
FIG. 3 is a perspective view of components of the system and the spine shown in FIG. 2.
Figure 4:
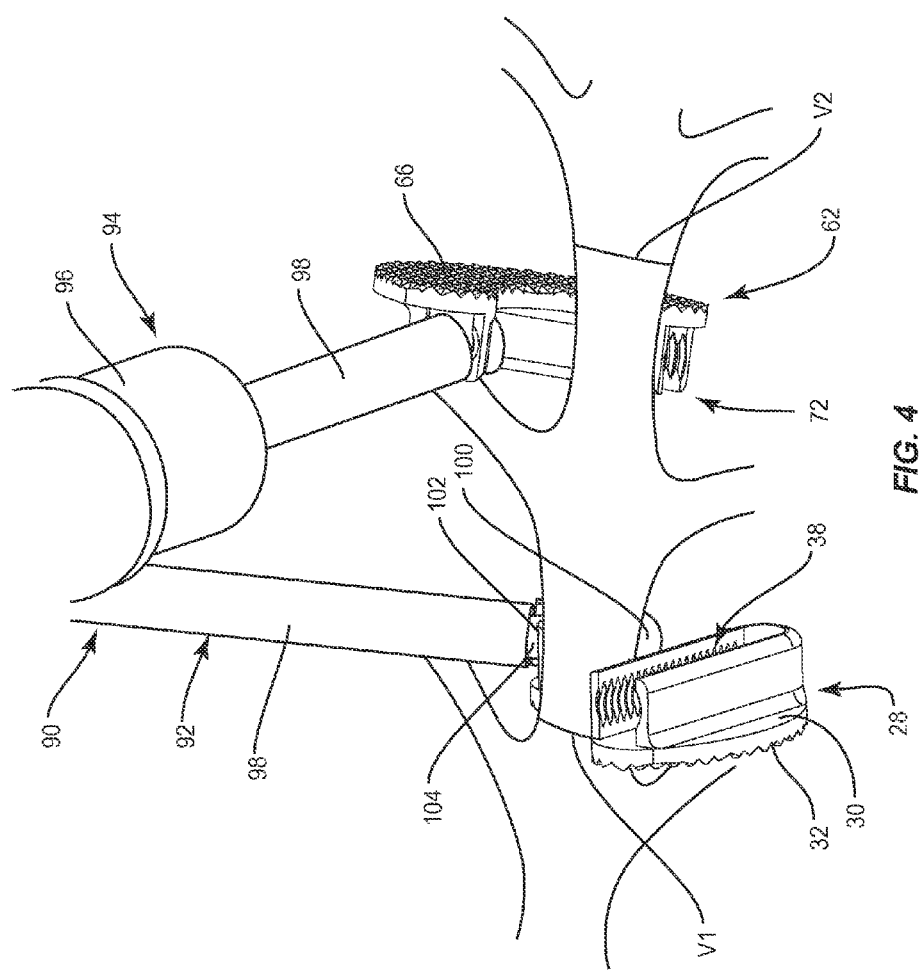
FIG. 4 is a perspective view of components of the system and the spine shown in FIG. 2.
Figure 5:
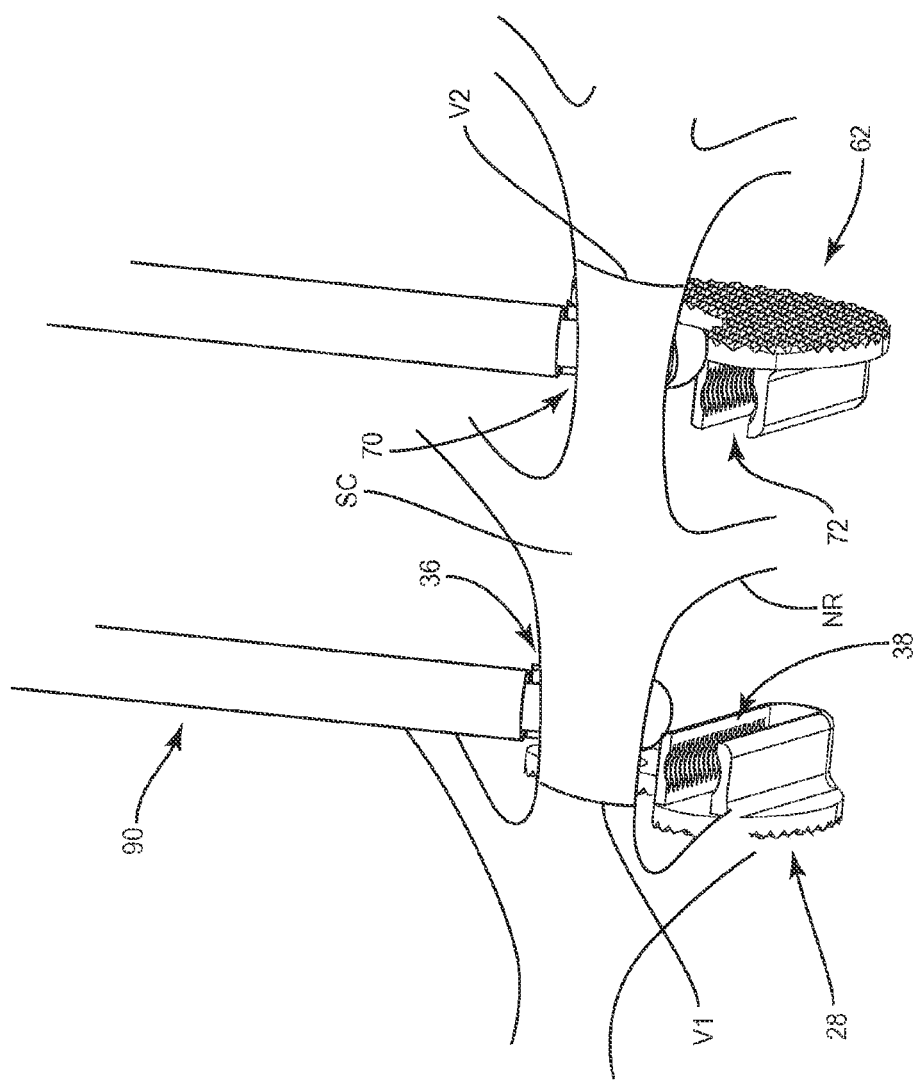
FIG. 5 is a perspective view of components of the system and the spine shown in FIG. 2.

In operation, delivery instrument 90 is matingly engaged to cavities 36, 70 of endplates 28, 62. Lock rod 104 of each manipulator 92, 94 is disposed in the second orientation to lock endplates 28, 62 between lock rod 104 and hook member 100. Handle 96 is gripped to deliver endplate 28 about vertebral tissue, such as, for example, at least one exiting nerve root NR and a spinal cord SC along a substantially posterior approach and to position endplate 28 adjacent vertebral surface E1 of vertebra V1, as shown in FIGS. 2 and 3. Endplate 62 is delivered about the at least one exiting nerve root NR and the spinal cord SC along a substantially posterior approach to position endplate 62 adjacent vertebral surface E1 of vertebra V2 such that cavities 36, 70 are disposed in substantial alignment and cavities 38, 72 are disposed in substantial alignment, as shown in FIGS. 4 and 5.

Figure 6:
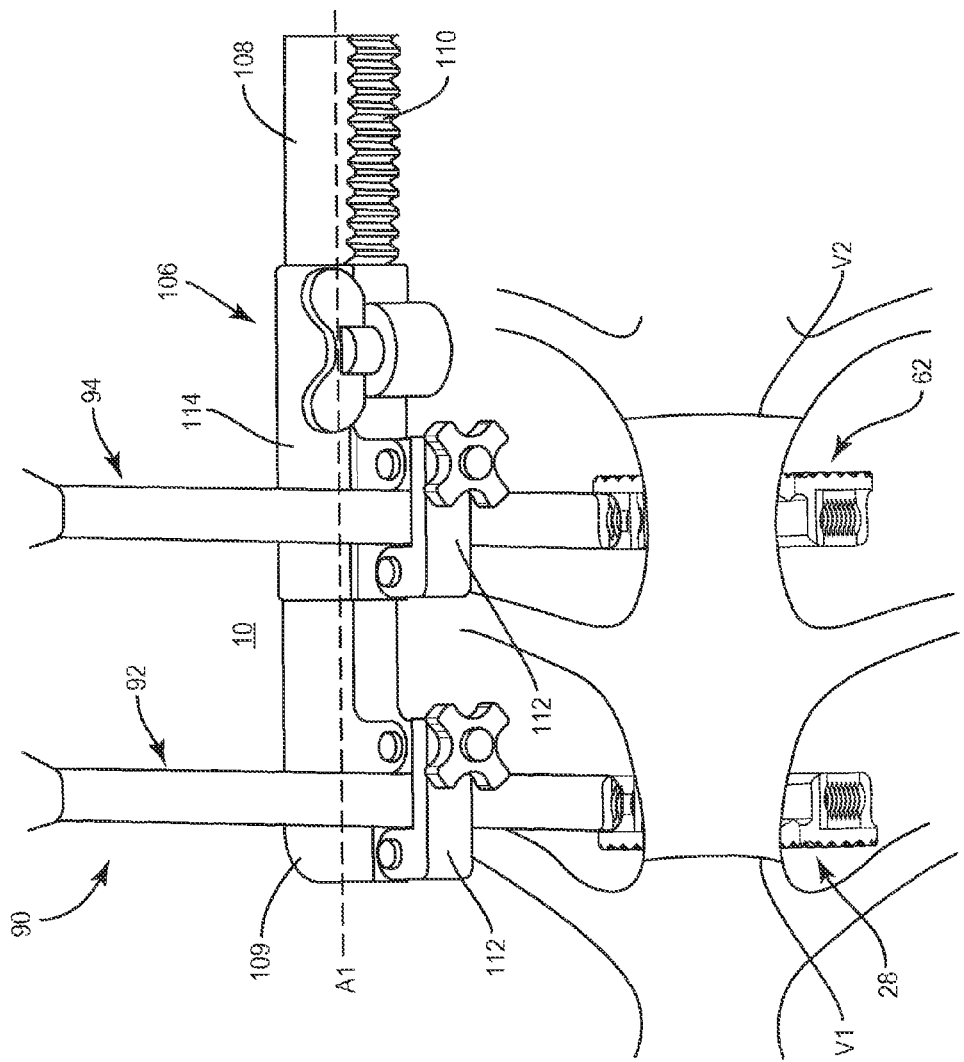
FIG. 6 is a perspective view of components of the system and the spine shown in FIG. 2.
Figure 7:
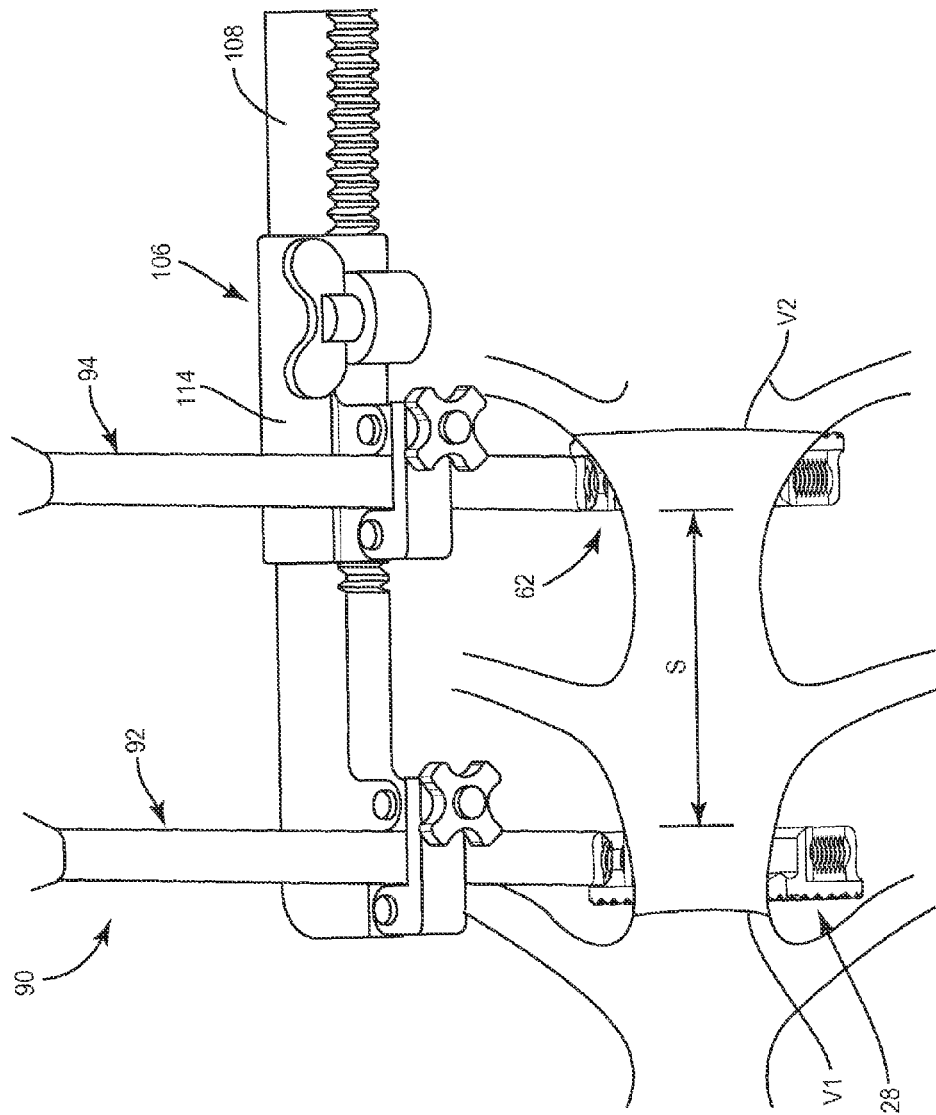
FIG. 7 is a perspective view of components of the system and the spine shown in FIG. 2.

Rack spreader 106 is engaged to delivery instrument 90 such that endplates 28, 62 are disposed in substantial alignment, as shown in FIG. 6. Rack spreader 106 is engaged to each manipulator 92, 94 of delivery instrument 90 and sleeve 114 is axially translated relative to gear rack 108 along axis A1. Endplates 28, 62 are spaced to apply a distracting force on vertebral surfaces E1, E1 to create space S, as shown in FIG. 7. Sleeve 114 is locked to gear rack 108 to fix space S between endplates 28, 62.

Figure 8:
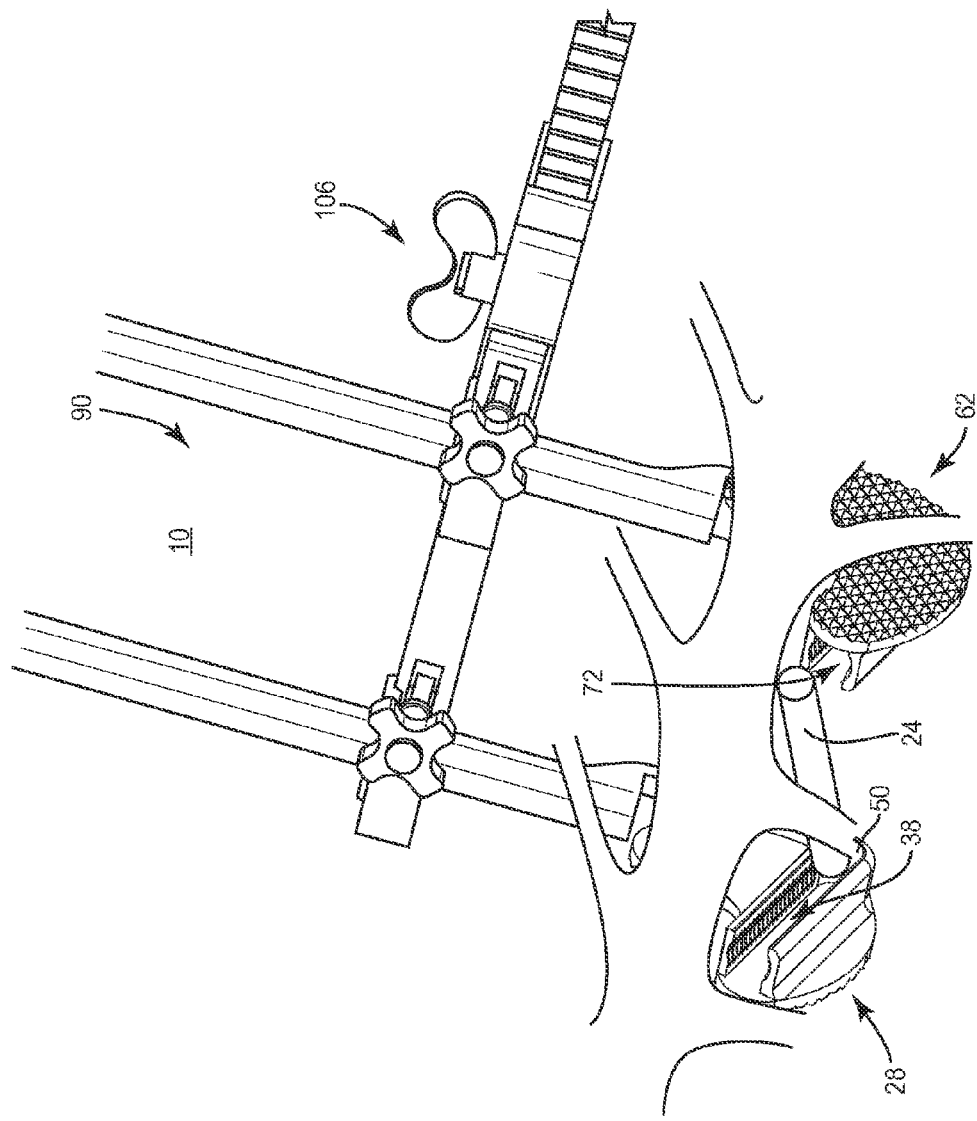
FIG. 8 is a perspective view of components of the system and the spine shown in FIG. 2.
Figure 9:
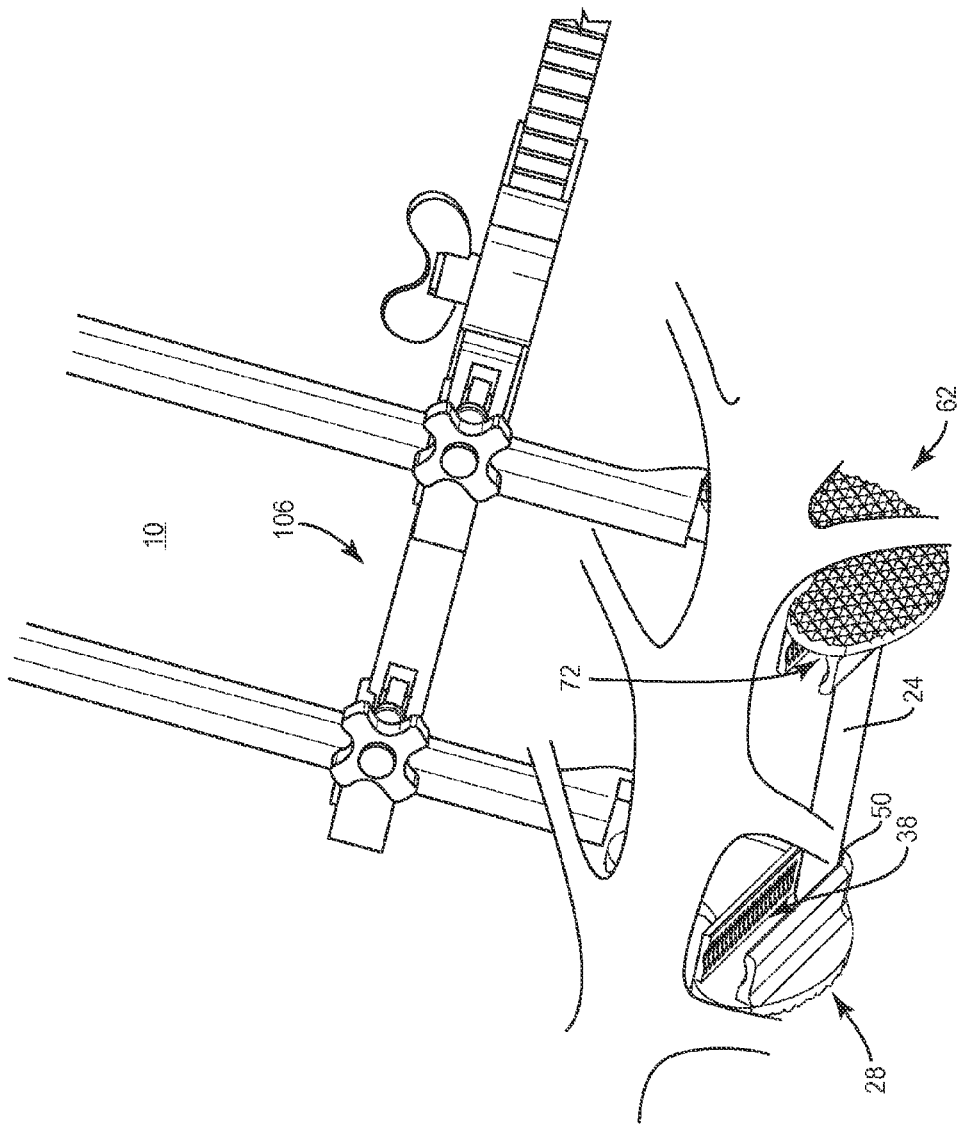
FIG. 9 is a perspective view of components of the system and the spine shown in FIG. 2.
Figure 10:
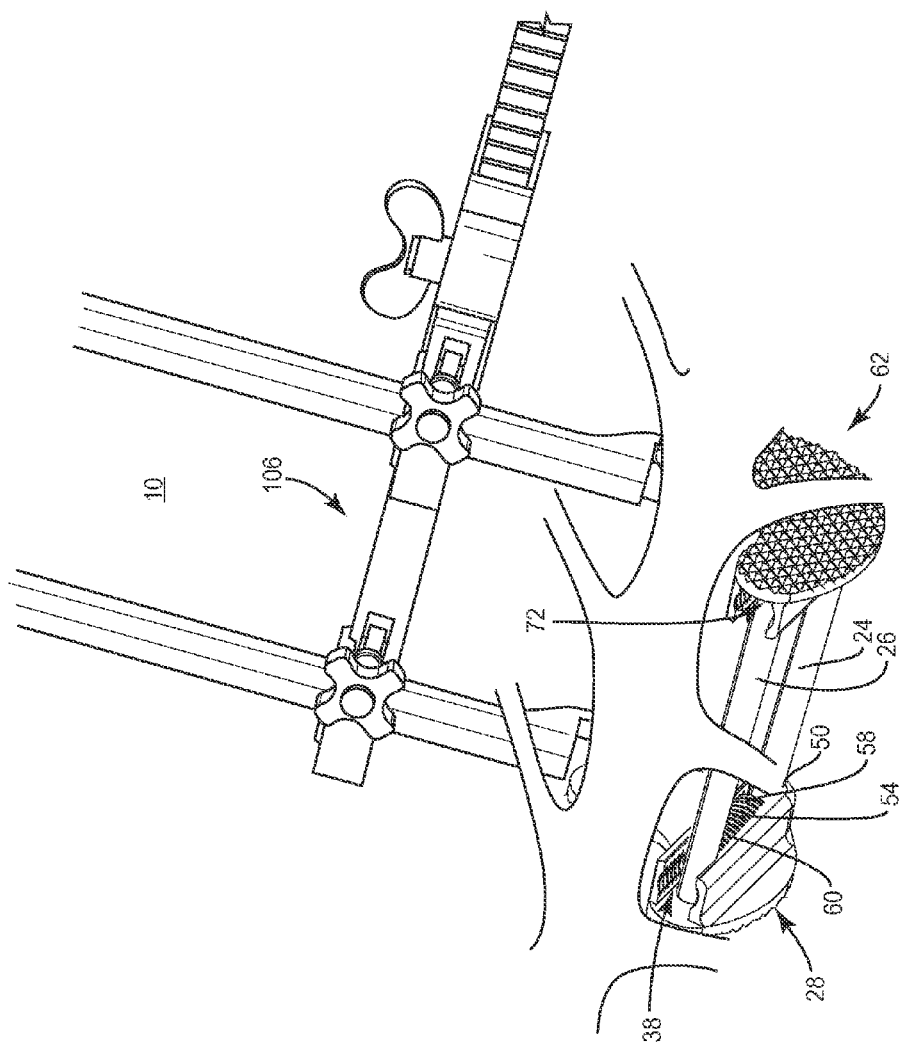
FIG. 10 is a perspective view of components of the system and the spine shown in FIG. 2.
Figure 11:
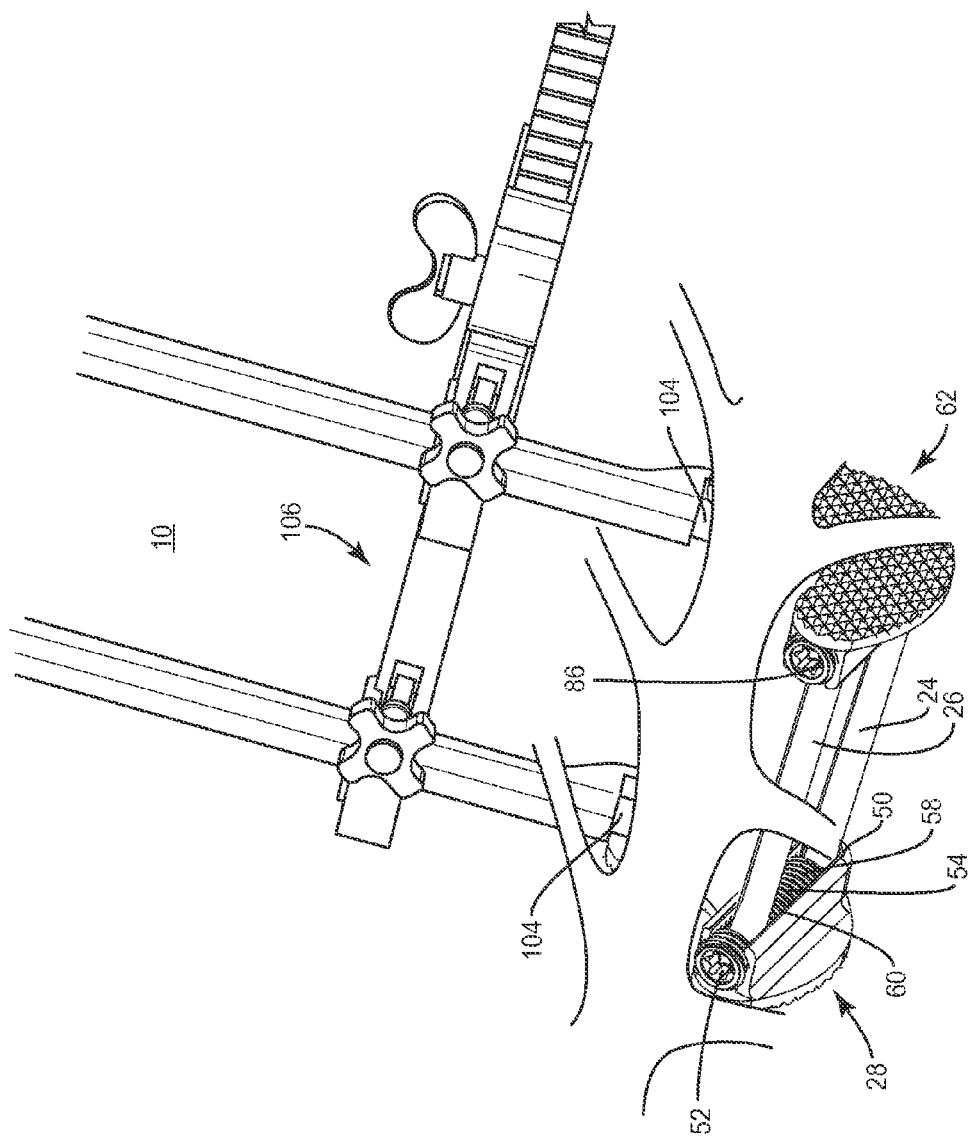
FIG. 11 is a perspective view of components of the system and the spine shown in FIG. 2.

The orientation of each endplate 28, 62 is locked in place and rod 24 is manipulated about nerve root NR to dispose rod 24 in cavities 38, 72 of each endplate 28, 62, as shown in FIG. 8. Opposite ends of rod 24 are disposed in passageways 50 of cavities 38, 72 of each endplate 28, 62, as shown in FIG. 9. Spacer 54 is axially translated through each of cavities 38, 72 into engagement with rod 24 such that rod 24 is fixed relative to endplates 28, 62, as shown in FIG. 10. Rod 26 is delivered about nerve root NR to position rod 26 within cavities 38, 72 adjacent ends 60 of spacers 54 of each endplate 28, 62, as shown in FIG. 10. Set screws 52, 86 are inserted within ends 46, 80 of cavities 38, 72 into engagement with opposite ends of rod 26 such that rod 26 is fixed between spacer 54 and set screws 52, 86, as shown in FIG. 11.

Figure 12:
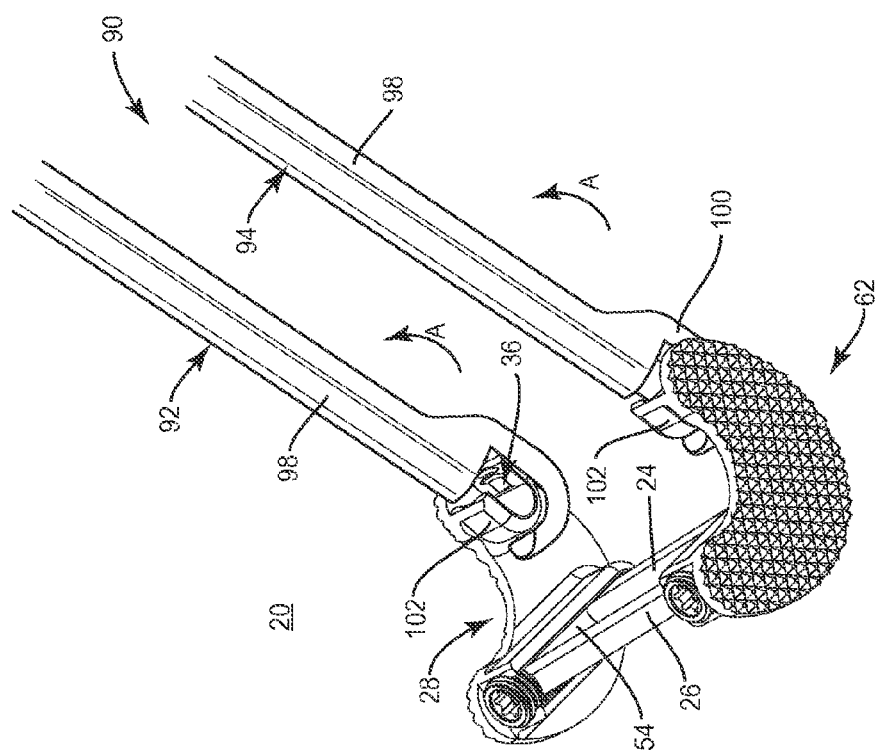
FIG. 12 is a perspective view of components of the system and the spine shown in FIG. 2.
Figure 13:
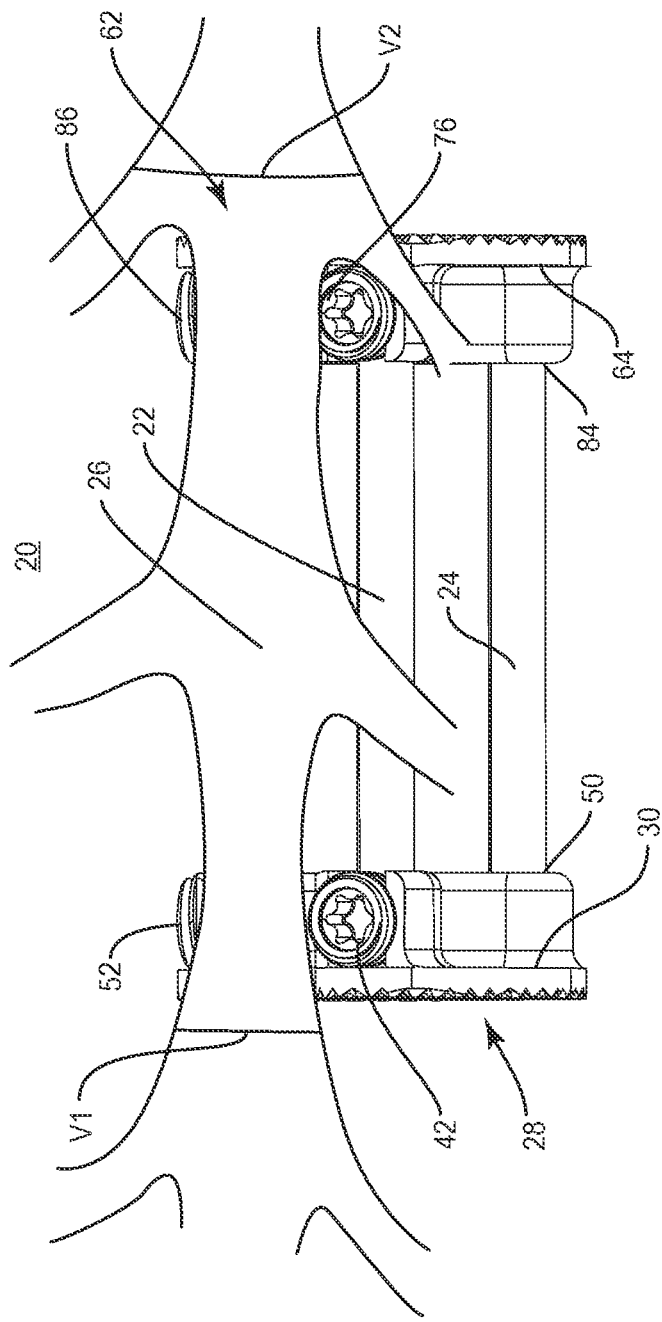
FIG. 13 is a perspective view of components of the system and the spine shown in FIG. 2.
Figure 14:
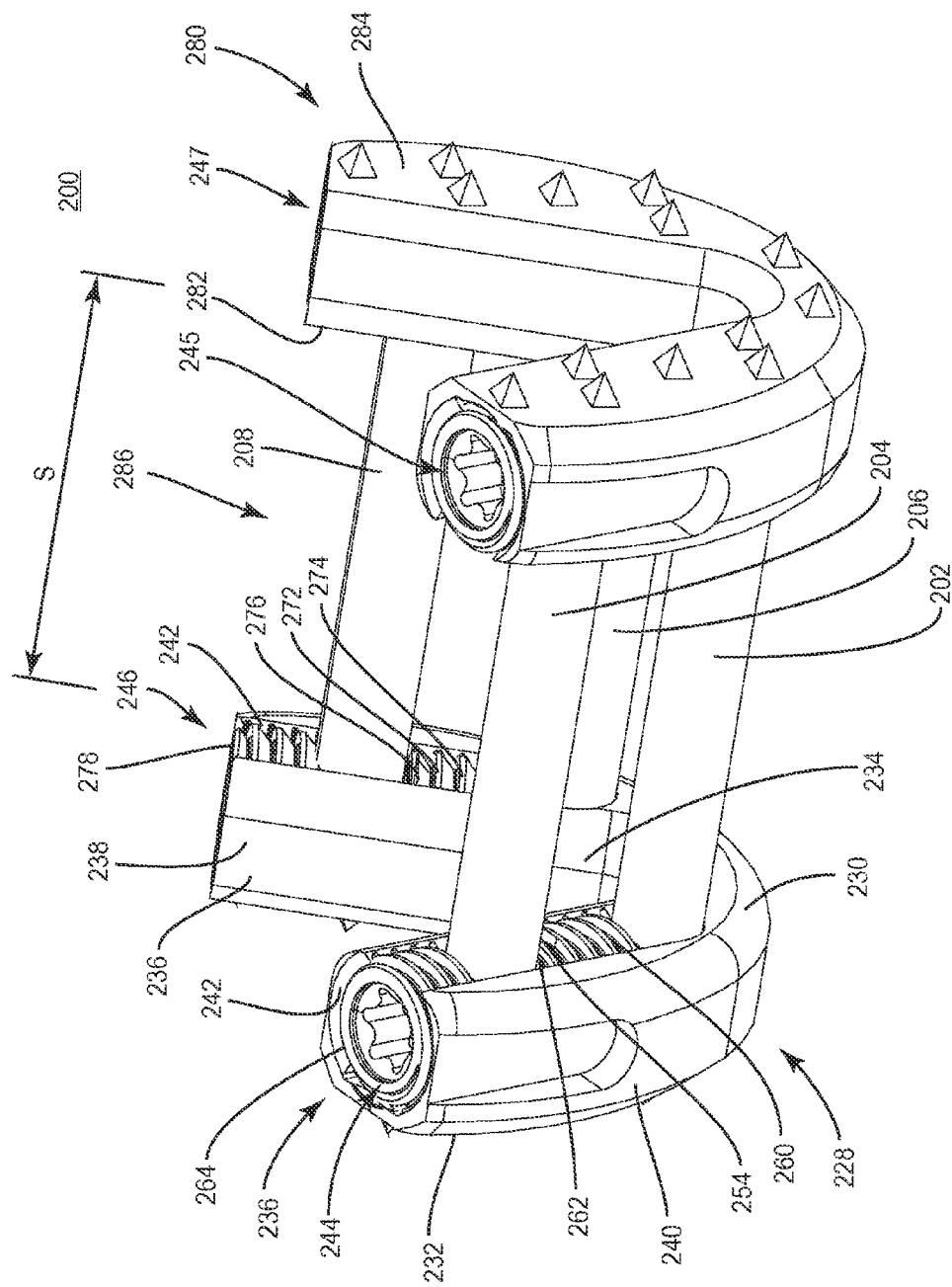
FIG. 14 is a perspective view of components of one embodiment of a spinal implant system in accordance with the principles of the present disclosure.

Lock rods 104 are withdrawn from cavities 36, 70 and manipulators 92, 94 are rotated, in the direction shown by arrow A in FIG. 12 to disengage hook members 100 from endplates 28, 62 and expose cavities 36, 70. Rod 22 is delivered about nerve root NR to position rod 22 in cavities 36, 70, as shown in FIG. 13. Set screws 42, 76 are inserted within cavities 36, 70 into engagement with opposite ends of rod 22 to fix rod 22 in cavities 36, 70 of each endplate 28, 62.

In one embodiment, endplates 28, 62 are spaced between vertebrae V such that endplate 28 engages vertebral surface E1 and endplate 62 engages vertebral surface E2 to restore vertebral spacing and provide distraction and/or restore mechanical support function. In one embodiment, spinal construct 20 is expanded, as discussed herein, progressively and/or gradually to provide an implant configured to adapt to the growth of a patient including the vertebrae. In some embodiments, the height of spinal construct 20 may also be decreased over a period of time and/or several procedures to adapt to various conditions of a patient.

In some embodiments, spinal construct 20 provides a footprint that improves stability and decreases the risk of subsidence into tissue. In some embodiments, spinal construct 20 provides height restoration between vertebral bodies, decompression, restoration of sagittal and/or coronal balance and/or resistance of subsidence into vertebral endplates.

Referring to FIGS. 2-13, in assembly, operation and use, system 10 including spinal construct 20, similar to that described with regard to FIG. 1, is employed with a surgical procedure, such as, for example, a lumbar corpectomy for treatment of a spine of a patient including vertebrae V. System 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of spinal construct 20.

System 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes vertebra V1 and vertebra V2. A diseased and/or damaged vertebra and intervertebral discs are disposed between the vertebrae V1 and V2. In some embodiments, spinal construct 20 is configured for insertion within a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from vertebral surface E1 of vertebra V1 and/or vertebral surface E2 of vertebra V2. Spinal construct 20 is provided with at least one agent, similar to those described herein, to promote new bone growth and fusion to treat the affected section of vertebrae V.

Spinal construct 20 is delivered to the surgical site adjacent vertebrae V with delivery instrument 90 including manipulators 92, 94 via the protected passageway for the arthrodesis treatment. Manipulators 92, 94 deliver endplates 28, 62 into the prepared vertebral space S, between vertebra V1 and vertebra V2.

Delivery instrument 90 is matingly engaged to cavities 36, 70 of endplates 28, 62. Lock rod 104 of each manipulator 92, 94 is disposed in the second orientation to lock endplates 28, 62 between lock rod 104 and hook member 100. Handle 96 is gripped to deliver endplate 28 about vertebral tissue, such as, for example, at least one exiting nerve root NR and a spinal cord SC along a substantially posterior approach and to position endplate 28 adjacent vertebral surface E1 of vertebra V1, as shown in FIGS. 2 and 3. Endplate 62 is delivered about nerve root NR and spinal cord SC along a substantially posterior approach to position endplate 62 adjacent vertebral surface E1 of vertebra V2 such that cavities 36, 70 are disposed in substantial alignment and cavities 38, 72 are disposed in substantial alignment, as shown in FIGS. 4 and 5.

Rack spreader 106 is engaged to delivery instrument 90 such that endplates 28, 62 are disposed in substantial alignment, as shown in FIG. 6. Rack spreader 106 is engaged to each manipulator 92, 94 of delivery instrument 90 and sleeve 114 is axially translated relative to gear rack 108 along axis A1. Endplates 28, 62 are spaced to apply a distracting force on vertebral surfaces E1, E1 to create space S, as shown in FIG. 7. Sleeve 114 is locked to gear rack 108 to fix space S between endplates 28, 62.

The orientation of each endplate 28, 62 is locked in place and rod 24 is manipulated about nerve root NR to dispose rod 24 in cavities 38, 72 of each endplate 28, 62, as shown in FIG. 8. Opposite ends of rod 24 are disposed in passageways 50 of cavities 38, 72 of each endplate 28, 62, as shown in FIG. 9. Spacer 54 is axially translated through each of cavities 38, 72 into engagement with rod 24 such that rod 24 is fixed relative to endplates 28, 62, as shown in FIG. 10. Rod 26 is delivered about nerve root NR to position rod 26 within cavities 38, 72 adjacent ends 60 of spacers 54 of each endplate 28, 62, as shown in FIG. 10. Set screws 52, 86 are inserted within ends 46, 80 of cavities 38, 72 into engagement with opposite ends of rod 26 such that rod 26 is fixed between spacer 54 and set screws 52, 86, as shown in FIG. 11.

Lock rods 104 are withdrawn from cavities 36, 70 and manipulators 92, 94 are rotated, in the direction shown by arrow A in FIG. 12, to disengage hook members 100 from endplates 28, 62 and expose cavities 36, 70. Rod 22 is delivered about nerve root NR to position rod 22 in cavities 36, 70, as shown in FIG. 13. Set screws 42, 76 are inserted within cavities 36, 70 into engagement with opposite ends of rod 22 to fix rod 22 in cavities 36, 70 of each endplate 28, 62.

Spinal construct 20 engages and spaces apart opposing vertebral surfaces E1, E2 and is secured within vertebral space S to stabilize and immobilize portions of vertebrae V in connection with bone growth for fusion and fixation of vertebrae V1, V2. Fixation of spinal construct 20 with surfaces E1, E2 may be facilitated by the resistance provided by the joint space and/or engagement with surfaces E1, E2. Rods 22, 24, 26 prevent endplates 28, 62 from axially translating relative to one another to fix spinal construct 20 in a selected expanded and/or contracted orientation, including those described herein.

In some embodiments, an agent(s), as described herein, may be applied to areas of the surgical site to promote bone growth. Components of system 10 including spinal construct 20 can be delivered or implanted as a pre-assembled device or can be assembled in situ. Components of system 10 including spinal construct 20 may be completely or partially revised, removed or replaced in situ. In some embodiments, one or all of the components of system 10 can be delivered to the surgical site via mechanical manipulation and/or a free hand technique.

In one embodiment, spinal construct 20 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, system 10 can be used with screws to enhance fixation. In some embodiments, system 10 and any screws and attachments may be coated with an agent, similar to those described herein, for enhanced bony fixation to a treated area. The components of system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

In one embodiment, as shown in FIGS. 14-19, system 10 includes a spinal construct 200, similar to spinal construct 20 described above with regard to FIGS. 1-13. Spinal construct 200 includes a plurality of longitudinal elements, such as, for example, a plurality of spinal rods 202, 204, 206, 208, similar to spinal rods 22, 24, 26 described above.

Figure 15:
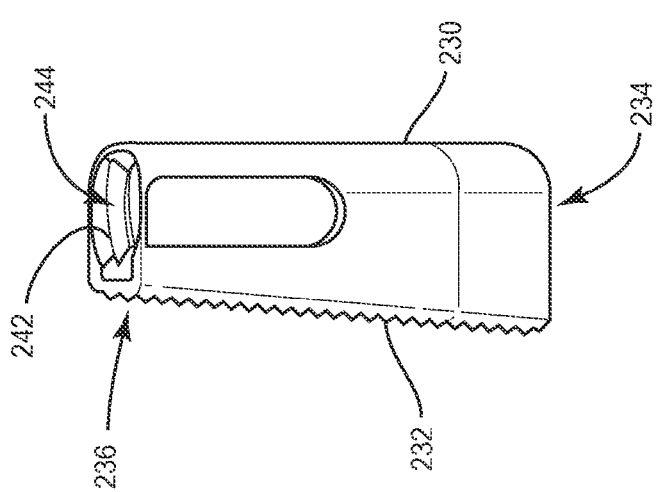
FIG. 15 is a lateral view of a component of the system shown in FIG. 14.
Figure 17:
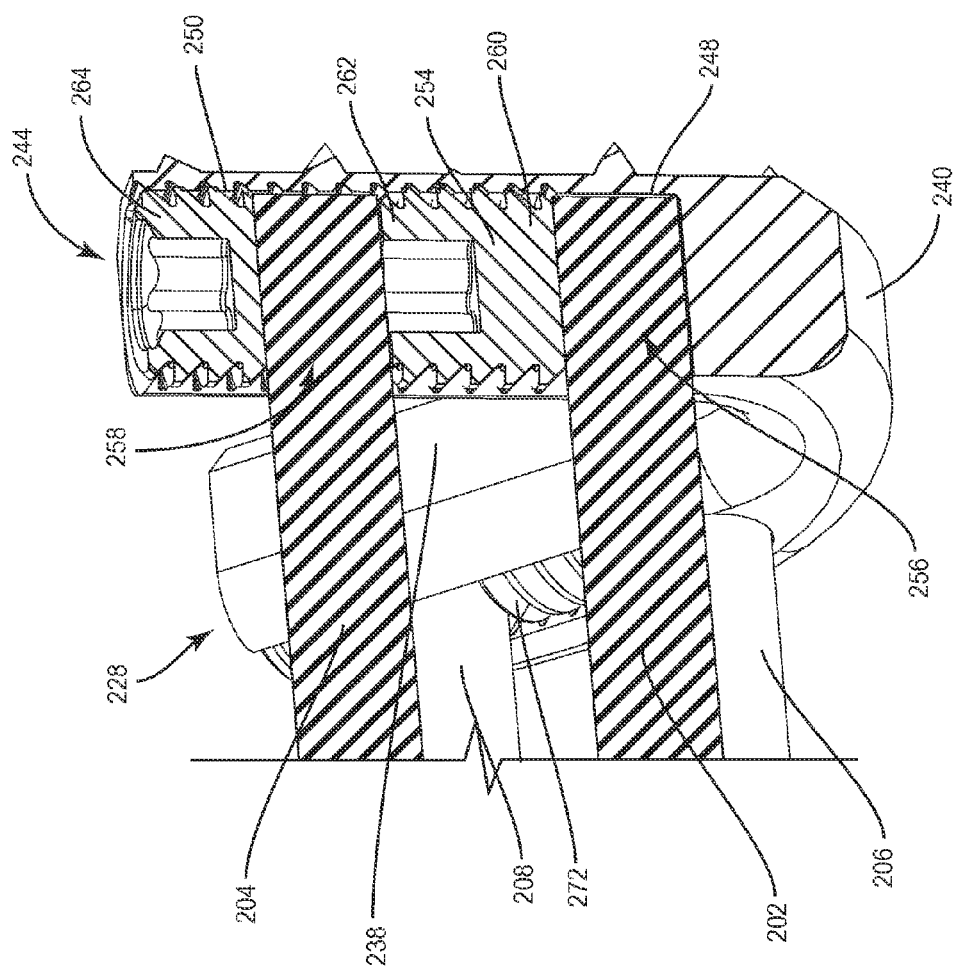
FIG. 17 is an enlarged breakaway view, in part cross section, of components of the system shown in FIG. 14.
Figure 18:
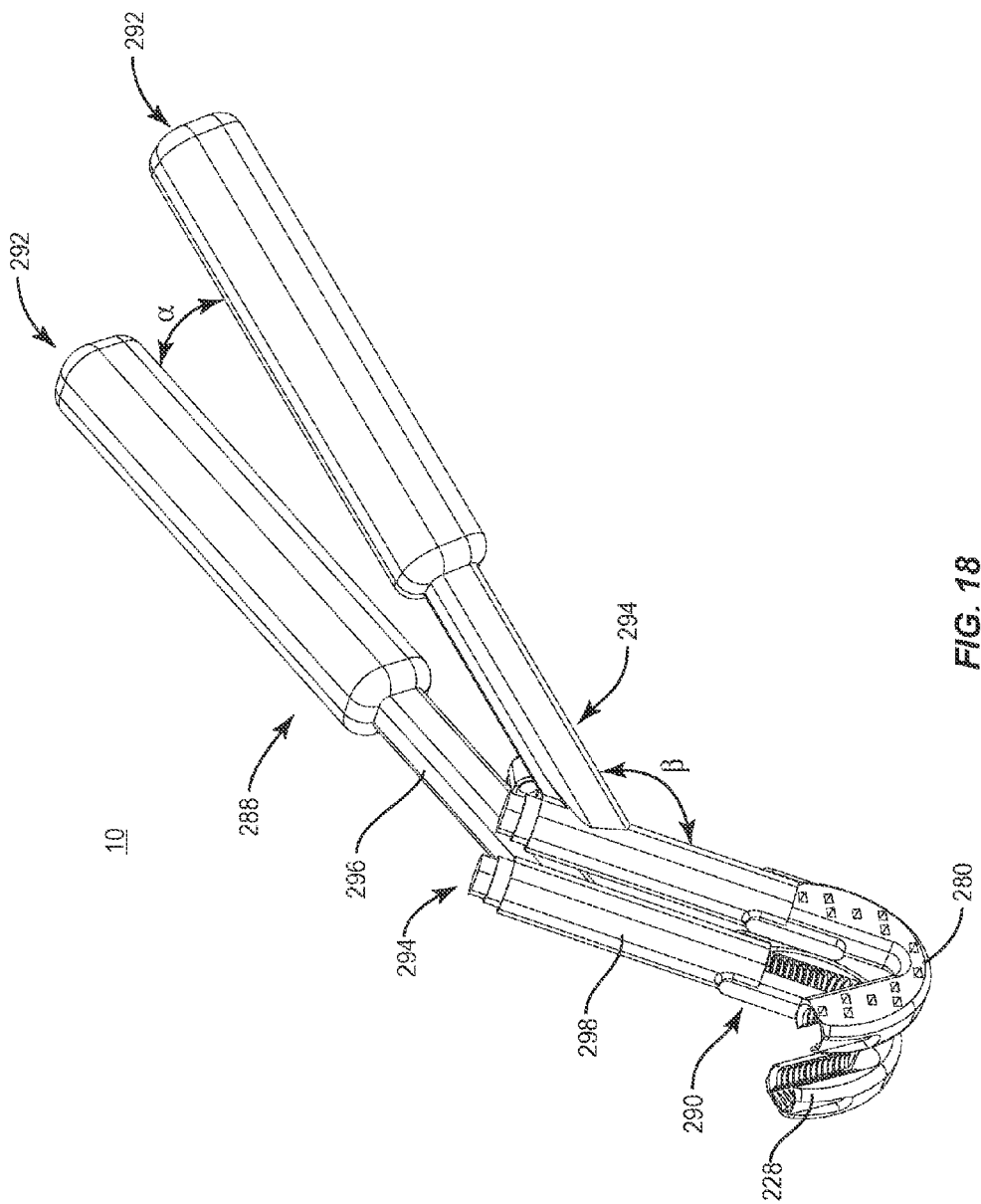
FIG. 18 is a perspective view of components of one embodiment of a spinal implant system in accordance with the principles of the present disclosure.
Figure 19:
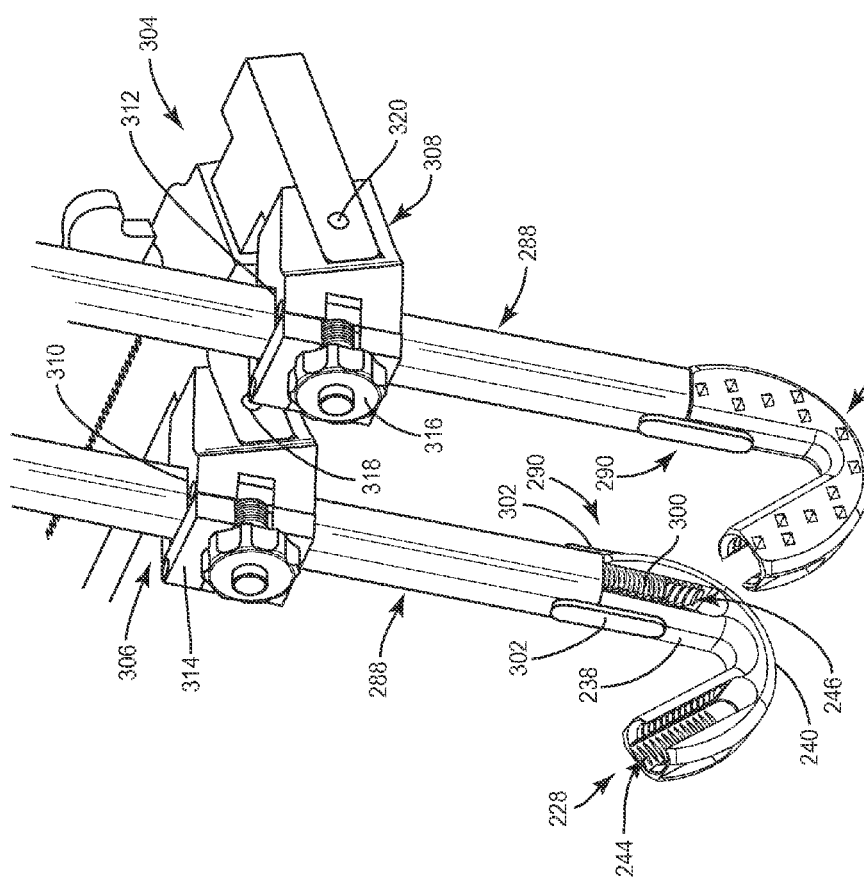
FIG. 19 is a perspective view of components of one embodiment of a spinal implant system in accordance with the principles of the present disclosure.

Spinal construct 200 includes a member, such as, for example, an endplate 228 having a U-shaped configuration, such as, for example, a parabolic configuration. In some embodiments, endplate 228 can alternatively include, for example, a V-shaped configuration, a J-shaped configuration and/or configuration to enable substantially posterior insertion around a spinal cord, provide peripheral zygapophyseal rim load bearing and/or a central cavity for graft contact with a vertebral surface. Endplate 228 includes a surface 230 and a surface 232 configured to engage a vertebral surface. Surface 232 is substantially planar and acutely angled relative to surface 230 to define a larger thickness at a lower portion 234 than an upper portion 236 of endplate 228, as shown in FIG. 15. In some embodiments, surface 232 may be disposed at alternate orientations, relative to surface 230, such as, for example, parallel, transverse, perpendicular and/or other angular orientations such as acute or obtuse, co-axial and/or may be offset or staggered. In some embodiments, surface 232 can have cross-hatch texturing, spikes, barbs, raised elements, a porous titanium coating, and/or be rough, textured, porous, semi-porous, dimpled and/or polished such that it facilitates engagement with tissue to enhance fixation. In one embodiment, spikes or screws are inserted through surfaces 230, 232 into engagement with tissue, such as, for example, vertebral tissue, to engage endplate 228 with the vertebral tissue to enhance fixation. Surfaces 230, 232 define a non-uniform thickness therebetween that tapers from lower portion 234 to upper portion 236 of endplate 228. In some embodiments, the thickness defined between surfaces 230, 232 is variously configured, such as, for example, irregular, uniform, offset, staggered, undulating, arcuate, and/or variable.

Figure 16:
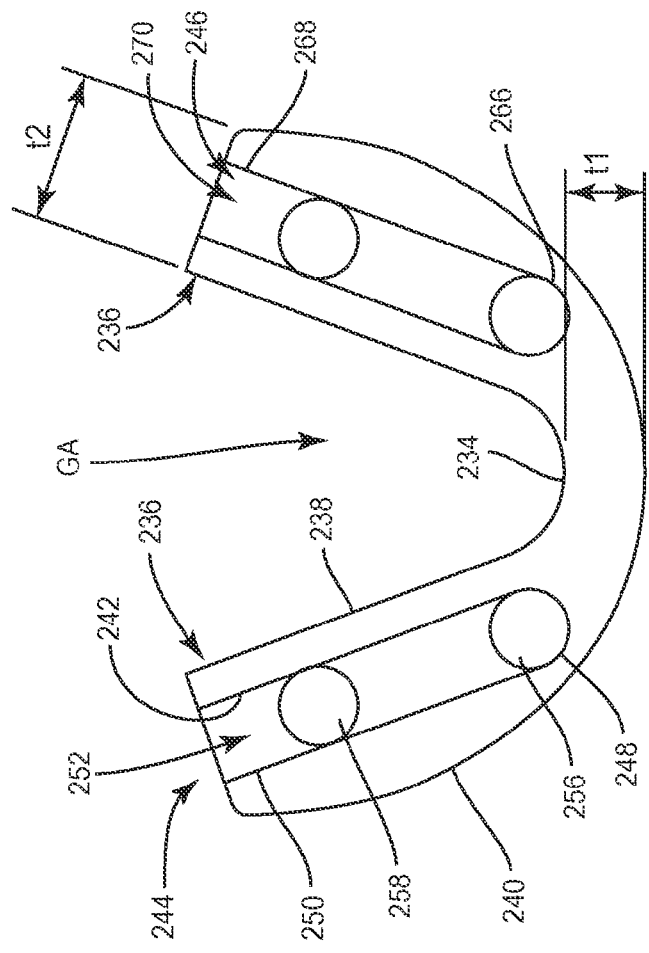
FIG. 16 is a side view of the components shown in FIG. 14.

Endplate 228 includes an inner sidewall 238 having a V-shaped cross section configuration and an outer sidewall 240 having a parabolic shaped cross section configuration, as shown in FIG. 16. In some embodiments, inner and outer sidewalls 238, 240 have alternate cross section configurations, such as, for example, U-shaped, parabolic-shaped, oval, oblong, triangular, square, polygonal, irregular, uniform, non-uniform, offset, staggered, undulating, arcuate, variable and/or tapered. Lower portion 234 has a thickness t1 defined between sidewalls 238, 240 that is less than a thickness t2 defined between sidewalls 238, 240 at upper portion 236 such that an enlarged graft area GA is provided.

Endplate 228 includes a surface, such as, for example, an inner surface 242 that defines a cavity 244 and a cavity 246. Cavities 244, 246 are disposed between surfaces 230, 232. Cavity 244 extends between an end 248 and an end 250 defining a linear passageway 252 therebetween. Passageway 252 includes an internal thread form configured for threaded engagement with a spacer 254, similar to spacer 54 described above, and a distal end of a delivery instrument, to be described below. In one embodiment, inner surface 242 can be alternatively partially threaded, non-threaded and/or passageway 252 has an arcuate configuration configured to align with the curvature of endplate 228 such that a spacer, as described herein, is smooth and/or square, oval or hexagonal, secures a spinal rod, which may also be smooth and/or square, oval or hexagonal. A plurality of spaced rods, such as, for example, rod 202 and rod 204 are disposed in the ends 248, 250 of cavity 244, respectively. In one embodiment, end 248 defines a first lateral recess 256 configured for disposal of rod 202 and end 250 defines a second lateral recess 258 configured for disposal of rod 204. Recesses 256, 258 have a circular cross section configuration corresponding to the cross section configuration of rods 202, 204 to capture rods 202, 204. In some embodiments, recesses 256, 258 have alternative cross section configurations, such as, for example, those alternatives described herein to capture variously shaped rods. In some embodiments, passageway 252 is configured for the spaced disposal of more than two rods, such as, for example, 3 to 10 rods. In some embodiments, passageway 252 is variously shaped, such as, for example, non-linear, arcuate, and/or the alternatives described herein.

Spinal construct 200 includes a spacer 254, similar to spacer 54 described above, disposable with passageway 252 between rods 202, 204 such that spacer 254 is fixed relative to inner surface 242 to fix rods 202, 204 relative to endplate 228. Spacer 254 includes a cylindrical element including an outer surface configured for fixation with inner surface 242 of endplate 228. Spacer 254 extends between an end 260 and an end 262. End 260 is engageable with rod 202 and end 262 is engageable with rod 204 such that spacer 254 is disposed between rods 202, 204 within passageway 252. Rod 202 is fixed to endplate 228 via engagement between surface 242 and end 260 of spacer 254. End 262 has a concave outer surface such that rod 204 is disposable in flush engagement with spacer 254. Spacer 254 has a length that occupies a substantial portion of passageway 252. In some embodiments, spacer 254 occupies a majority of passageway 252. A coupling member, such as, for example, a set screw 264, shorter in length than spacer 254, is disposed to engage rod 204 within cavity 244. Set screw 264 is matingly engageable with end 250 of cavity 244 such that rod 204 is secured between end 262 of spacer 254 and set screw 264.

Cavity 246, similar to cavity 244 described above, extends between an end 266 and an end 268 defining a linear passageway 270 therebetween, similar to linear passageway 252 described above. A plurality of spaced rods, such as, for example, rod 206 and rod 208 are disposed in ends 266, 268 of cavity 246, respectively. An end 274 of a spacer 272, similar to spacer 254 described above, is engageable with rod 206. An end 276 of spacer 272 is engageable with rod 208 such that spacer 272 is disposed between rods 206, 208 within passageway 270. Rod 206 is fixed to endplate 228 via engagement between surface 242 and end 274 of spacer 272. End 276 of spacer 272 has a concave outer surface such that rod 208 is disposable in flush engagement with spacer 272. A coupling member, such as, for example, a set screw 278 is disposed to engage rod 208 within cavity 246. Set screw 278 is matingly engageable with end 268 of cavity 246 such that rod 208 is secured between end 276 of spacer 272 and set screw 278.

Spinal construct 200 includes a member, such as, for example, an endplate 280, similar to endplate 228 described above. Endplate 280 includes a surface 282 and a surface 284 configured to engage a second vertebral surface. Surfaces 230, 282 of endplates 228, 280 are oriented to face one another. Rods 202, 204, 206, 208 are disposed between surfaces 230, 282 of endplates 228, 280 such that endplates 228, 280 are spaced to create and maintain a space S between the first and second vertebral surfaces. Cavities 244, 245 of endplates 228, 280 are disposed in substantial alignment such that spaced rods 202, 204 are disposed in cavities 244 of each endplate 228, 280. Cavities 246, 247 of endplates 228, 280 are disposed in substantial alignment such that spaced rods 206, 208 are disposed in cavities 246, 247. Rods 202, 204, 206, 208 are oriented with endplates 228, 280 to define a graft cavity 286 therebetween. Graft cavity 286 is configured to receive an agent, similar to the agent described above.

Spinal implant system 10 includes a delivery instrument, such as, for example, angled inserters 288 configured for mating engagement with each of cavities 244, 245 and/or cavities 246, 247 of endplates 228, 280 via a tongue in groove connection 290. Inserters 288 include a pair of splayed handles 292. Splayed handles 292 are offset from one another at an angle α. In some embodiments, angle α may include an angle in a range of approximately 5 to 50 degrees. In some embodiments, splayed handles 292 are variously angled, such as, for example, acute or obtuse, co-axial and/or may be offset or staggered. The angle between handles 292 allows endplates 228, 280 to be initially disposed immediately adjacent one another between vertebrae. Inserters 288 include arms 294 extending from splayed handles 292 and including a proximal portion 296 and a distal portion 298. Proximal portion 296 is connected to handles 292. Distal portion 298 is matingly engageable with endplates 228, 280 via tongue in groove connection 290. Distal portion 298 is obtusely angled with respect to proximal portion 296 and handles 292 at an angle β. In some embodiments, angle β may include an angle in a range of approximately 70 to 170 degrees. The angle between distal portion 298 and handles 292 allows for easier manipulation of inserters 288 around the spinal cord and associated anatomy. Tongue in groove connection 290 includes a threaded lock 300 and a pair of tabs 302. Threaded lock 300 is configured for threaded engagement with at least one of cavities 244, 245, 246, 247 of each endplate 228, 280. The pair of tabs 302 are disposable with detents in inner and outer sidewalls 238, 240 of endplates 228, 280 such that distal portion 298 is matingly engageable with each of cavities 244, 245 and/or cavities 246, 247 of endplates 228, 280. In some embodiments, distal portion 298 is detachably fastened to endplates 228, 280 by various fastening engagements, such as, for example, frictional engagement, threaded engagement, mutual grooves, screws and/or nails.

System 10 includes a distractor, such as, for example, a rack spreader 304, similar to rack spreader 106 described above. Rack spreader 304 is engageable with proximal portion 296 or distal portion 298 of inserters 288 such that inserters 288 are angled relative to rack spreader 304. Rack spreader 304 includes a coupling member 306 and a coupling member 308. Coupling members 306, 308 each include an inner surface defining cavities 310 and 312 configured for disposal of inserters 288. Coupling members 306, 308 further include latch locks 314, 316 for capturing inserters 288 in cavities 310, 312. Coupling members 306, 308 are pivotally connected to rack spreader 304 at pivot points 318, 320 such that an angle between rack spreader 304 and inserters 288 is adjustable. Rack spreader 304 axially translates inserters 288 causing the distraction and/or compression of vertebral surfaces via a distracting and/or compressing force applied by endplates 228, 280.

Figure 20:
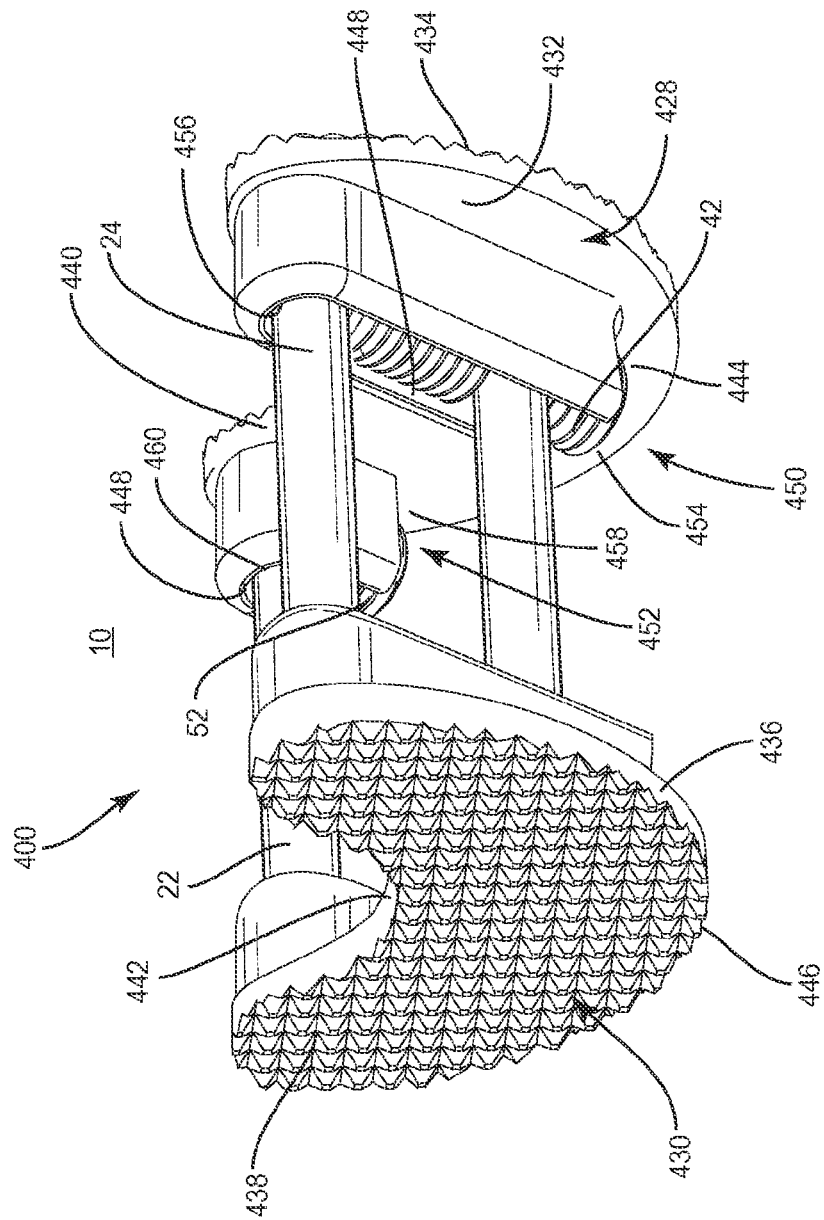
FIG. 20 is a perspective view of components of one embodiment of a spinal implant system in accordance with the principles of the present disclosure.
Figure 21:
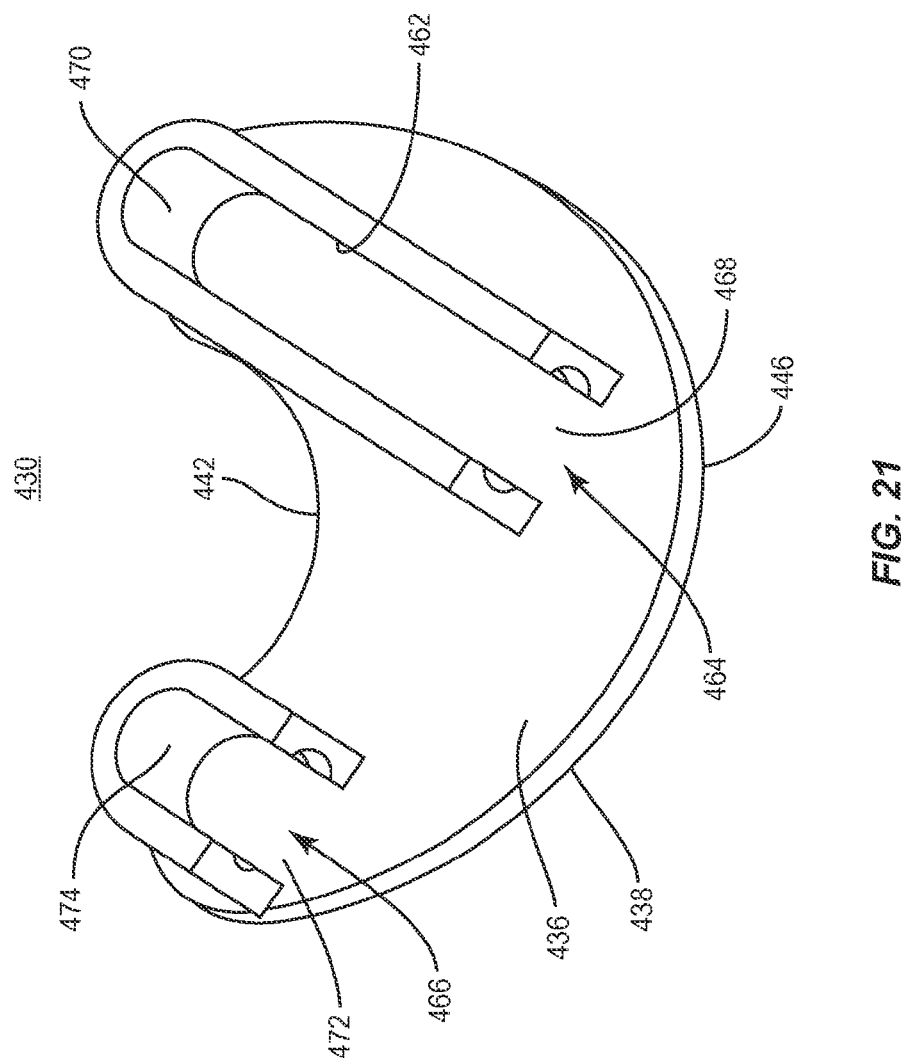
FIG. 21 is a perspective view of components of the system shown in FIG. 20.

In one embodiment, as shown in FIGS. 20 and 21, system 10 includes a spinal construct 400, similar to spinal construct 20 described herein with regard to FIGS. 1-13. Spinal construct 400 is used in spinal surgery, such as, for example, an anterior vertebrectomy such that a patient is positioned on a side and access to the spine is between the lower ribs. Spinal construct 400 includes members, such as, for example, endplates 428, 430, similar to endplates 28, 62 described herein with regard to FIGS. 1-13. Endplate 428 includes a surface 432 and a surface 434 configured to engage a vertebral surface of a vertebral body. Endplate 430 includes a surface 436 and a surface 438 configured to engage a vertebral surface of a vertebral body. Endplates 428, 430 each include upper, outer arcuate surfaces 440, 442 and lower, outer arcuate surfaces 444, 446. Endplates 428, 430 have a U-shaped configuration, such as, for example, a parabolic configuration defined by the upper and lower surfaces 440, 442, 444, 446.

Endplate 428 includes a surface, such as, for example, an inner surface 448 that defines a cavity 450 and a cavity 452, similar to cavities 36, 38 described herein with regard to FIGS. 1-13. Cavity 450 includes an anterior opening 454 configured for insertion of set screw 42 and a U-shaped passageway 456 configured for disposal of rod 24. Cavity 450 is oriented relative to surface 432 such that opening 454 is disposed adjacent lower surface 444 and U-shaped passageway 456 is oriented adjacent upper surface 440. Cavity 452 includes an anterior opening 458 configured for insertion of set screw 52 and a U-shaped passageway 460 configured for disposal of rod 22. Cavity 452 is oriented relative to surface 432 such that opening 458 is disposed adjacent lower surface 444 and U-shaped passageway 460 is oriented adjacent upper surface 440.

Endplate 430 includes a surface, such as, for example, an inner surface 462 that defines a cavity 464 and a cavity 466, similar to cavities 36, 38 described herein with regard to FIGS. 1-13. Cavity 464 includes an anterior opening 468 configured for insertion of a set screw (not shown) and a U-shaped passageway 470 configured for disposal of rod 24. Cavity 464 is oriented relative to surface 436 such that opening 468 is disposed adjacent lower surface 446 and U-shaped passageway 470 is oriented adjacent upper surface 442. Cavity 466 includes an anterior opening 472 configured for insertion of a set screw (not shown) and a U-shaped passageway 474 configured for disposal of rod 22. Cavity 466 is oriented relative to surface 436 such that opening 472 is disposed adjacent lower surface 446 and U-shaped passageway 474 is oriented adjacent upper surface 442. In some embodiments, spinal construct 400 is manipulated for insertion into a spine along a substantially anterior approach for treatment of the spine such that openings 454, 458 of endplate 428 and openings 468, 472 of endplate 430 are oriented in an anterior direction relative to a body of a patient, for receiving the set screws.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
a first member including a first cradle that defines a first cavity and a second cradle that defines a second cavity, the first member being configured to engage a first vertebral surface, the first cavity defining a longitudinal axis that intersects the second cradle;
a second member including a surface that defines a first cavity and a second cavity, the second member being configured to engage a second vertebral surface; and
at least one spacer,
wherein the members are spaced and the first cavities are disposed in substantial alignment such that at least one first rod is disposed in the first cavities and the second cavities are disposed in substantial alignment such that a plurality of second rods are disposed in the second cavities and spaced via the at least one spacer disposed between the second rods within at least one of the second cavities.

2. A spinal construct as recited in claim 1, wherein the spacer is fixed relative to the surface of the second member to fix the second rods relative to the second member.

3. A spinal construct as recited in claim 1, wherein the spacer is disposed between the second rods within each of the second cavities and fixed with the surface of the second member, and further comprising a coupling member disposed to engage a second rod within each of the second cavities.

4. A spinal construct as recited in claim 1, wherein the second member further includes a U-shaped configuration having a parabolic configuration.

5. A spinal construct as recited in claim 1, wherein the first member has a U-shaped configuration.

6. A spinal construct as recited in claim 1, wherein at least one of the second cavities includes a linear passageway.

7. A spinal construct as recited in claim 1, wherein each of the first cavities is configured for disposal of only one first rod.

8. A spinal construct as recited in claim 1, wherein:
the cradles extend outwardly from an inner surface of the first member;
the inner surface and outer surfaces of the cradles define an end portion of a graft cavity, the end portion being positioned between the outer surfaces; and
the rods are oriented with the members to define a middle portion of the graft cavity that is continuous with the end portion.

9. A spinal implant system comprising:
a delivery instrument; and
the spinal construct recited in claim 1, wherein each of the first cavities is configured for mating engagement with the delivery instrument, the delivery instrument comprising an arm having a hook member configured for disposal about an outer surface of each of the first cavities, the arm comprising a lock rod positionable between a first orientation such that the lock rod is disposed with the arm and a second orientation such that the lock rod protrudes from the arm for disposal in one of the first cavities such that the delivery instrument captures one of the members between the lock rod and the hood member.

10. A method for treating a spine disorder, the method comprising the steps of:
providing the spinal construct recited in claim 1;
delivering the first member about vertebral tissue along a substantially posterior approach and adjacent a first vertebral surface;
delivering the second member about the vertebral tissue along a substantially posterior approach and adjacent a second vertebral surface such that the first cavities are disposed in substantial alignment and the second cavities are disposed in substantial alignment;
spacing the members;
disposing at least one first rod in the first cavities; and
disposing a plurality of spaced second rods within the second cavities.

11. A method as recited in claim 10, wherein the vertebral tissue includes nerve roots and spinal cord.

12. A method as recited in claim 10, wherein the step of disposing the plurality of spaced second rods includes disposing a spacer between the second rods within each of the cavities.

13. A spinal construct as recited in claim 1, wherein:
the at least one spacer extends between a first end and an opposite second end that includes a concave outer surface; and
the concave outer surface engages one of the second rods for disposal thereof in flush engagement with the at least one spacer disposed between the second rods.

14. A spinal construct as recited in claim 1, wherein the second cavity of the first member has a maximum length that is greater than that of the first cavity of the first member and the second cavity of the second member has a maximum length that is greater than that of the first cavity of the second member.

15. A spinal implant system comprising:
a first endplate including a first cradle that defines a first cavity and a second cradle that defines a second cavity, the first endplate being configured to engage a first vertebral surface, the first cavity defining a longitudinal axis that intersects the second cradle;
a second endplate including a surface that defines a first cavity and a second cavity, the second endplate being configured to engage a second vertebral surface;
a plurality of first rods;
a plurality of second rods; and
a plurality of spacers,
wherein the endplates are spaced and the first cavities are disposed in substantial alignment such that the first rods are spaced via the spacers in the first cavities and the second cavities are disposed in substantial alignment such that the second rods are spaced via the spacers in the second cavities.

16. A spinal implant system as recited in claim 15, further comprising a plurality of coupling members disposed to engage the rods in the cavities for fixation of the rods with the endplates, wherein each of the spacers include a cylindrical element including a threaded outer surface configured for fixation with threaded surfaces of the cradles.

17. A spinal implant system as recited in claim 15, further comprising a delivery instrument configured for mating engagement with each of the first cavities.

18. A spinal implant system as recited in claim 17, wherein the delivery instrument is matingly engageable with each of the first cavities via a tongue in groove connection.

19. A spinal implant system as recited in claim 17, wherein the delivery instrument includes a pair of splayed handles.

20. A spinal construct comprising:
a first member including a body and first and second arms that extend from the body, the first member comprising a first cradle positioned on the first arm that defines a first cavity and a second cradle positioned on the body and the second arm that defines a second cavity, the first member being configured to engage a first vertebral surface;
a second member including a surface that defines a first cavity and a second cavity, the second member being configured to engage a second vertebral surface; and
at least one spacer,
wherein the members are spaced and the first cavities are disposed in substantial alignment such that at least one first rod is disposed in the first cavities and the second cavities are disposed in substantial alignment such that a plurality of second rods are disposed in the second cavities and spaced via the at least one spacer disposed between the second rods within at least one of the second cavities.

* * * * *